United States Patent [19]

Brennan et al.

[11] 4,338,443
[45] Jul. 6, 1982

[54] SYNTHESIS OF N-(2-HYDROXYETHYL)PIPERAZINE

[75] Inventors: Michael E. Brennan; George P. Speranza, both of Austin, Tex.

[73] Assignee: Texaco Inc., White Plains, N.Y.

[21] Appl. No.: 178,339

[22] Filed: Aug. 15, 1980

[51] Int. Cl.$^3$ .......................................... C07D 295/08
[52] U.S. Cl. .................................................. 544/401
[58] Field of Search ................. 544/401, 358; 564/480

[56] References Cited

U.S. PATENT DOCUMENTS

| | | | |
|---|---|---|---|
| 2,636,033 | 4/1953 | Malkemas | 544/401 |
| 2,910,477 | 10/1959 | Long, Jr. | 544/358 |
| 3,037,023 | 5/1962 | Moss et al. | 544/358 |
| 3,383,417 | 5/1968 | Lichtenwalter | 544/401 |

OTHER PUBLICATIONS

Elderfield, "Heterocyclic Compounds", vol. 6, (1960), p. 429.

*Primary Examiner*—Anton H. Sutto
*Attorney, Agent, or Firm*—Carl G. Ries; Robert A. Kulason; James L. Bailey

[57] ABSTRACT

N-(2-hydroxyethyl)piperazine is prepared by carrying out a reductive alkylation and cyclization reaction of monoethanolamine and diethanolamine in presence of a hydrogen atmosphere and a hydrogenation-dehydrogenation catalyst.

1 Claim, No Drawings

SYNTHESIS OF N-(2-HYDROXYETHYL)PIPERAZINE

BACKGROUND OF THE INVENTION

1. Field of the Invention

This invention relates to a process for making N-(2-hydroxyethyl)piperazine.

2. Prior Art

Triethylenediamine, a valuable polyurethane catalyst is usually made from N-(2-hydroxyethyl)piperazine. This latter material in turn is normally prepared by reacting ethylene oxide with a large excess of piperazine. However, the unreacted piperazine must be recovered via recycle and this is a difficult, expensive and time-consuming process.

It would therefore be an advance in the art if a new process of making N-(2-hydroxyethyl)piperazine were discovered via a reaction scheme which does not involve the use of piperazine.

It therefore becomes an object of the invention of providing a new and improved scheme of preparing N-(2-hydroxyethyl)piperazine which avoids the use of piperazine as a reactant. Other objects will appear hereinafter.

SUMMARY OF THE INVENTION

This invention involves a method for preparing N-(2-hydroxyethyl)piperazine. In brief, the process comprises the step of effecting a simultaneous reductive alkylation-cyclization reaction of monoethanolamine and diethanolamine in presence of a hydrogen atmosphere and a hydrogenation-dehydrogenation catalyst. The resultant N-(2-hydroxyethyl)piperazine may then be recovered by conventional techniques.

DESCRIPTION OF PREFERRED EMBODIMENTS OF THE INVENTION

The method of the invention is generally carried out by charging monoethanolamine and diethanolamine to a reaction vessel in presence of hydrogen and a hydrogenation-dehydrogenation catalyst and heating the reaction mixture under pressure for sufficient amount of time to effect the desired conversion.

The mol ratio of monoethanolamine to diethanolamine may be widely varied in carrying out the reaction. Usually the ratio varies from 10:1 to 1:10, more preferably from 3:1 to 1:3. In a typical case 3 mols of monoethanolamine are reacted per mol of diethanolamine.

Again the reaction may be effected with or without benefit of solvent. When a solvent is employed usually water is utilized as a solvent. Other hydrophilic solvents such as methanol, ethanol, isopropyl alcohol etc., or hydrophobic solvents such as benzene, xylene, toluene, etc. may be employed.

The catalysts useful in the practice of this invention are conventional hydrogenation-dehydrogenation catalysts. Preferred are those hydrogenation-dehydrogenation catalysts containing at least one of the metals nickel, cobalt, copper, or their oxides. Nickel and cobalt are the preferred metals and the catalyst can contain minor amounts of normally nonreducible metal oxides, such as, for example, chromium oxide, molybdenum oxide, manganese oxide or thorium oxide. The preferred catalyst is one containing nickel, copper and chromium as described, for example, in U.S. Pat. No. 3,152,988. This preferred catalyst is prepared by the reduction of a mixture of the oxides of nickel, copper and chromium in the presence of hydrogen at a temperature within the range of about 250° to 400° C. Calculated on an oxide-free basis, the catalyst usually contains from 60 to 85 mol percent nickel, 14 to 37 mol percent copper and 1 to 5 mol percent chromium. A particularly preferred catalyst composition is one containing 70 to 80 mol percent nickel, 20 to 25 mol percent copper and 1 to 5 mol percent chromium. Raney nickel catalyst is also a preferred catalyst for the practice of this invention.

The process of this invention is conducted at a temperature of from about 100° C. to about 300° C. with a preferred range being from about 125° C. to about 225° C. Most preferably, the temperature is 150°–190° C. The pressure at which this reaction is carried out is from about 200 to about 4,000 psig with from 300 to about 1500 psig being the preferred range. Most preferably, the pressure of reaction is 300–800 psig.

The pressure for the reaction is usually provided by the addition of sufficient hydrogen to the closed reactor so that the reaction system remains in the liquid phase.

The catalytic reaction carried out here in the presence of hydrogen, can be either carried out in a closed batch system or continuously, such being only a matter of design within the capabilities of the skilled engineer.

This invention will be further illustrated by the following examples which should not be construed to be limiting thereof.

EXAMPLES 1–4

A clean and dry 1-1 stirred stainless steel autoclave was charged with a reaction solution of monoethanolamine and diethanolamine, water, and powdered nickel-copper-chromia catalyst. The catalyst contained about 75 mol percent nickel, 23 mol percent copper and 2 mol percent chromium. The reaction mass was purged well with hydrogen and then pressured to 250 psig with hydrogen, heated to the desired temperature and held 2.0 hours. After cooling to room temperature the autoclave was carefully vented and the product mixture recovered. Results in the Table below are based on GLC analysis and Karl Fisher water determination.

TABLE I

| Run No. | Temp., °C. | Max. Press., psig | Conversion | | | % Selectivity HEP (1) |
|---|---|---|---|---|---|---|
| | | | MEA | DEA | Total | |
| 183.2g (3 moles) monoethanolamine (MEA), 105.1g (1.0 mole) diethanolamine (DEA), 144.2g water, 25.0g catalyst | | | | | | |
| 1 | 200 | 585 | 90.8 | 29.5 | 71.4 | 24.6 |
| 2 | 190 | 510 | 79.1 | 1.9 | 54.7 | 32.3 |
| 274.9g (4.5 moles) MEA, 157.7g (1.5 moles) DEA, 37.5g catalyst | | | | | | |
| 3 | 200 | 565 | 83.1 | 10.7 | 59.8 | 25.6 |
| 4 | 190 | 490 | 60.8 | — | 39.8 | 34.5 |

(1) Hydroxyethyl piperazine

Here runs were carried out in a continuous 25 ml microreactor containing 24 ml of the catalyst of Examples 1–4. The reactor was operated at 2500 psig, 12 ml/hr of MEA/DEA (mol ratio of 2) feed and 12 l/hr of H$_2$. Results are in Table II below.

TABLE II

| Run No. | Temp. | % Conversion | | | % Selectivity | | |
|---|---|---|---|---|---|---|---|
| | | MEA | DEA | TOTAL | PIP(1) | HEP | BHEP(2) |
| 5 | 170° C. | 48.9 | 26.3 | 39.7 | 17.4 | 42.2 | 26.8 |
| 6 | 180° C. | 56.6 | 36.1 | 48.2 | 13.4 | 34.8 | 26.5 |
| 7 | 190° C. | 62.5 | 55.8 | 59.8 | 12.9 | 25.1 | 19.0 |

(1) Piperazine
(2) Bishydroxyethyl piperazine

From the foregoing, one of ordinary skill in the art will be able to practice the invention herein and make obvious modifications therefrom without departing from the scope of the invention as set forth in the appended claims.

The invention is hereby claimed as follows:

1. A method for the synthesis of N-(2-hydroxyethyl)-piperazine which comprises the step of effecting a simultaneous reductive alkylation-cyclization reaction of monoethanolamine and diethanolamine at a temperature of 125°–250° C. and under a pressure range of 300–800 psig in presence of a hydrogen atmosphere and a hydrogenation-dehydrogenation catalyst comprising 60 to 85 mol percent nickel, 14 to 37 mol percent copper, and 1–5 mol percent chromium.

* * * * *